US008499633B2

(12) United States Patent
Hampton et al.

(10) Patent No.: US 8,499,633 B2
(45) Date of Patent: Aug. 6, 2013

(54) NON-CONTACT ULTRASONIC TESTING METHOD AND DEVICE FOR CERAMIC HONEYCOMB STRUCTURES

(75) Inventors: Leslie Eugene Hampton, Corning, NY (US); Zhiqiang Shi, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 1052 days.

(21) Appl. No.: 11/435,650

(22) Filed: May 16, 2006

(65) Prior Publication Data
US 2007/0266789 A1 Nov. 22, 2007

(51) Int. Cl.
*G01N 29/04* (2006.01)

(52) U.S. Cl.
USPC .......................................................... 73/596

(58) Field of Classification Search
USPC .............................. 73/596–600, 602, 614–633
See application file for complete search history.

(56) References Cited

U.S. PATENT DOCUMENTS

| 3,813,926 | A | * | 6/1974 | Stubbeman | 73/609 |
| 4,319,840 | A | | 3/1982 | Kondo et al. | 356/241 |
| 4,752,895 | A | * | 6/1988 | Sarr | 702/39 |
| 4,869,944 | A | | 9/1989 | Harada et al. | 428/116 |
| 5,056,368 | A | | 10/1991 | Kawasaki et al. | 73/642 |
| 5,062,911 | A | * | 11/1991 | Hampton et al. | 156/89.14 |
| 6,367,330 | B1 | * | 4/2002 | Schafer | 73/598 |
| 6,372,677 | B1 | | 4/2002 | Nose et al. | 501/119 |
| 6,457,363 | B1 | * | 10/2002 | Schafer | 73/596 |
| 6,666,070 | B1 | * | 12/2003 | Hagg et al. | 73/38 |
| 6,840,083 | B2 | * | 1/2005 | Hijikata | 73/12.01 |
| 6,843,130 | B2 | * | 1/2005 | Georgeson | 73/600 |

(Continued)

FOREIGN PATENT DOCUMENTS

| JP | 63-263467 | * | 10/1988 |
| JP | 7-244026 | * | 9/1995 |

(Continued)

OTHER PUBLICATIONS

Peters et al., "Resonant Transmission of Air-Coupled Ultrasound Through Metallic Inserts in Honeycomb Sandwich Structures", CP760, Review of Quantitative Nondestructive Evaluation, vol. 24, 2005 American Institute of Physics, 0-7354-0245-0/05, pp. 1026-1032.

(Continued)

*Primary Examiner* — Helen Kwok
(74) *Attorney, Agent, or Firm* — Charles A. Greene; Joseph M. Homa

(57) ABSTRACT

Both a method and apparatus for determining internal discontinuities or inhomogeneities in a green or fired ceramic honeycomb structure is provided. In the method of the invention, an ultrasonic transmitter is positioned adjacent to, but not in contact with, the honeycomb structure. The transmitter propagates an ultrasonic wave, of preferably less than 5 MHz, through the honeycomb structure which is received, filtered and analyzed to determine the presence or absence of internal discontinuities or inhomogenieties. The ultrasonic transmitter generates an ultrasonic wave of less than five megahertz to provide a relatively high signal-to-noise ratio in the ultrasonic wave propagated through the structure. The device of the invention may include an array of ultrasonic transmitters and receivers that generate simultaneously transmit and receive ultrasonic signals throughout the ceramic honeycomb structure as it is moved relative to the array such that the structure is quickly and efficiently scanned for discontinuities or inhomogenieties.

6 Claims, 13 Drawing Sheets

U.S. PATENT DOCUMENTS

| | | | |
|---|---|---|---|
| 6,938,409 B2* | 9/2005 | Birckigt et al. | 60/275 |
| 6,964,694 B2* | 11/2005 | Rauchfuss et al. | 95/1 |
| 7,012,678 B2* | 3/2006 | Enomoto et al. | 356/237.1 |
| 7,276,101 B2* | 10/2007 | Ichikawa | 55/523 |
| 2002/0039964 A1 | 4/2002 | Tanaka et al. | 502/304 |
| 2004/0031386 A1* | 2/2004 | Rauchfuss et al. | 95/1 |
| 2004/0047994 A1* | 3/2004 | Becker et al. | 427/346 |
| 2005/0247131 A1* | 11/2005 | Breuer | 73/579 |
| 2007/0144260 A1* | 6/2007 | Fei et al. | 73/596 |
| 2007/0199380 A1 | 8/2007 | Daoud | 73/596 |

FOREIGN PATENT DOCUMENTS

| | | | |
|---|---|---|---|
| JP | 2004-151078 | * | 5/2004 |
| JP | 2006-106011 | | 4/2006 |
| WO | 2005/095932 | | 10/2005 |

OTHER PUBLICATIONS

Sun et al., "NDT Technologies for Ceramic Matrix Composites: Oxide and Nonoxide", Submitted Oct. 2005, Materials Evaluation, Jan. 2006, pp. 52-60.

M. Asmani et al, "Influence of porosity on Young's modulus and Poisson's ration in alumina ceramics", Journal of the European Ceramic Society, vol. 21 (2001), pp. 1081-1086.

L.-S. Chang et al, "Characterization of alumina ceramics by ultrasonic testing", Materials Characterization, vol. 45 (2000), pp. 221-226.

Hyunjo Jeong et al, "Quantitative estimation of material properties of porous ceramics by means of composite micromechanics and ultrasonic velocity", NDT&E International, vol. 29, No. 2, 1996, pp. 95-101.

L.P. Martin et al, "Effect of particle size distribution upon specific surface area and ultrasonic velocity in sintered ceramic powders", Materials Science and Engineering, vol. A246 (1998), pp. 151-160.

A.K. Mukhopadhyay et al, "An analysis of microstructural parameters in the minimum contact area model for ultrasonic velocity-porosity relations", Journal of the European Ceramic Society, vol. 20 (2000), pp. 29-38.

Byoung-Chul Shin et al, "Ultrasonic transducers for continuous-cast billets", Sensors and Actuators, vol. A51 (1996), pp. 173-177.

Alexander Wanner, "Elastic modulus measurements of extremely porous ceramic materials by ultrasonic phase spectroscopy", Materials Science and Engineering, vol. A248 (1998), pp. 35-43.

* cited by examiner

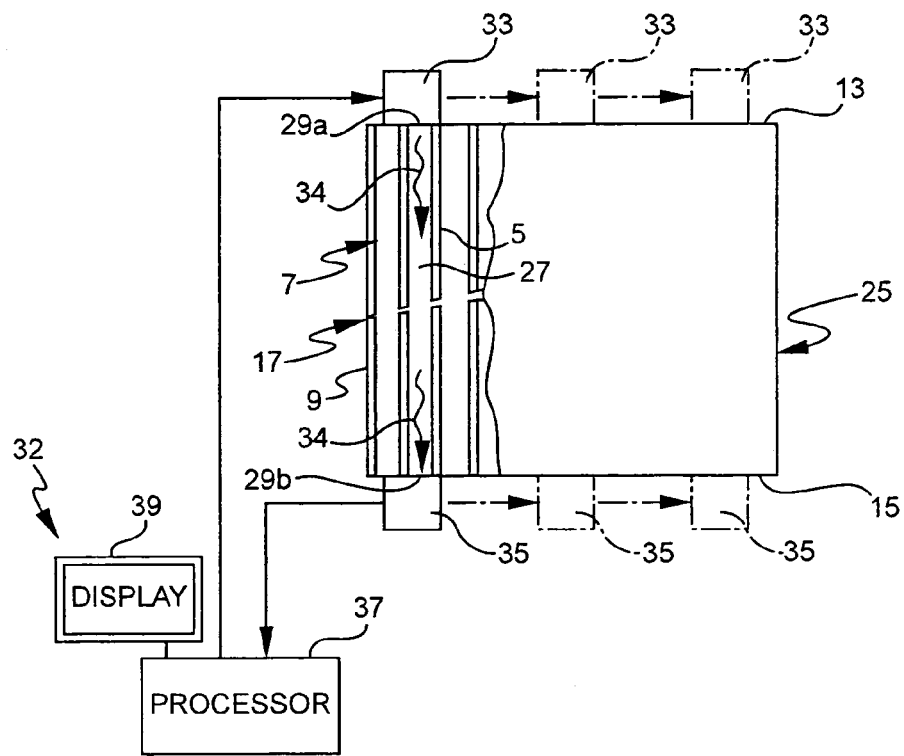
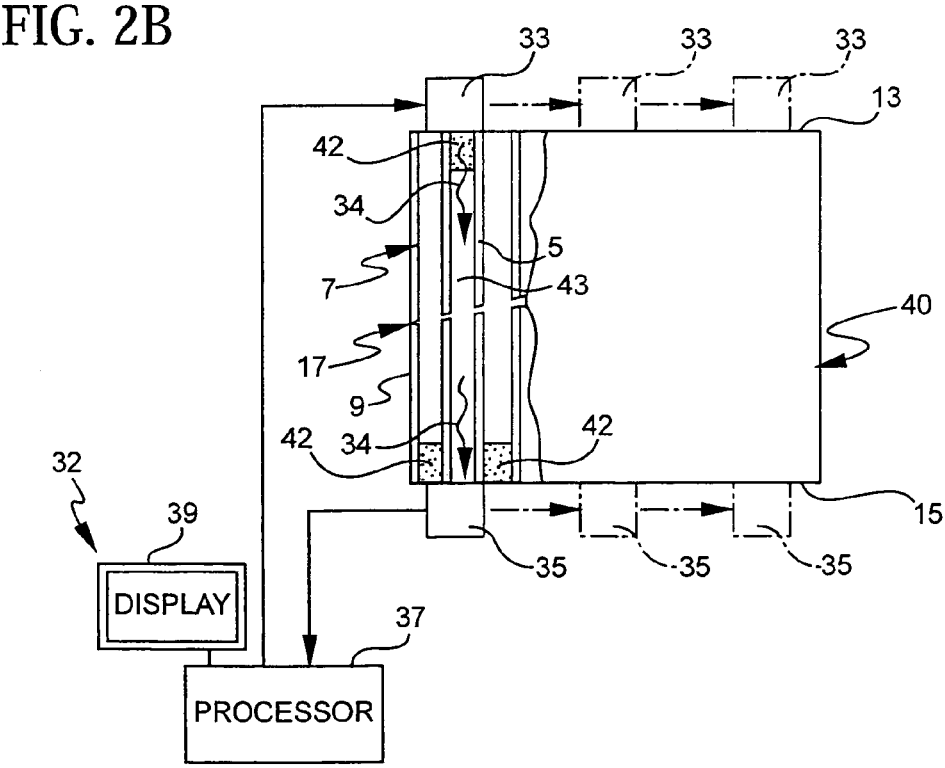

NON-CONTACT ULTRASONIC TESTING METHOD AND DEVICE FOR CERAMIC HONEYCOMB STRUCTURES

FIELD OF THE INVENTION

This invention generally relates to methods for detecting internal defects in ceramic honeycomb structures, and is specifically concerned with an ultrasonic testing method and device that quickly and efficiently determines presence or absence of internal defects within such structures.

BACKGROUND OF THE INVENTION

Ceramic honeycomb structures are used in vehicular exhaust systems to reduce pollutants. Such structures generally comprise a network of interconnected web walls that form a matrix of elongated, gas-conducting cells which may be square, octagonal or hexagonal in shape, for example. The network of web walls is surrounded by a cylindrical outer skin that is integrally connected to the outer edges of the web walls to form a can-or oval-shaped structure having opposing inlet and outlet ends for receiving and expelling exhaust gases through the matrix of cells.

Such ceramic honeycomb structures may be used as either particulate filters in the exhaust systems of diesel-powered automobiles or other equipment, or as automotive catalytic converters. When used as particulate filters, the open ends of the cells on the inlet and outlet ends of the structure are preferably plugged in "checkerboard" fashion such that exhaust gases entering the inlet end of the structure must pass through the porous, ceramic web walls before they are allowed to exit the open ends of the cells at the outlet end of the structure. When used as catalytic converters, the cells remain unplugged so that the exhaust gases may flow directly through them, and the cell walls are coated with a precious metal catalyst containing platinum, rhodium, or palladium for example. After the web walls reach a required light-off temperature, the catalyst impregnated over the web walls oxidizes $CO_2$, and disassociates $NO_x$ into $N_2$ and $O_2$. Both applications of ceramic honeycomb structures are important in reducing pollutants that would otherwise be expelled into the environment.

Such ceramic structures may be formed by extruding a paste-like, ceramic precursor to cordierite, mullite, silicon carbide, or aluminum titanate through a die to simultaneously form the network of web walls along with the integrally-connected outer skin. The resulting extruded, green body is cut, dried and moved to a kiln which converts the green ceramic body into a fired ceramic body. The fired body may be then either plugged in the aforementioned pattern to form a diesel particulate filter, or subjected to a catalyst wash coat in order to impregnate the walls of the flow-through cells with the catalyst.

Unfortunately, during the extrusion, handling and firing procedures, internal damage can occur within the ceramic substrate which can compromise the performance of the body in removing pollutants from the automotive exhaust system where it ultimately resides. Such damage can include cracks oriented along the axis of rotation of the structure and cracks transverse to this axis, referred to hereinafter as axial cracks and "ring-off" cracks. Still other damage is manifested by a localized separation between the network of web walls, and the outer skin of the structure. Finally, external hairline cracks on the surface of the structure can occur, or other strength-compromising scratches and deformities.

Methods for testing various manufactured parts for discontinuities are also known in the prior art. Such methods include x-ray inspection and CT scans. However, such x-ray inspections are insensitive to the internal cracks which may exist within honeycomb ceramic structures unless the defect is larger than a certain size. Even when the defect is sufficiently large to be detected, the x-ray image must be examined carefully for fine details in order to discern such defects. The time to completely inspect one honeycomb structure can take hours, which is far too long to be used in connection with a practical manufacturing process. Other techniques based on the same principle as an x-ray inspection, such as laminography and tomography suffer from the same drawbacks, in that they require far too much time and effort to be able to effectively and reliably detect cracks and other discontinuities within a time frame suited to a practical manufacturing process.

Clearly, what is needed is a method for inspecting ceramic honeycomb structures which is capable of quickly and reliably detecting the presence or absence of such discontinuities as axial or "ring-off cracks", skin separations, hairline cracks on the exterior, or other deformities or faults that could seriously compromise the function of the ceramic structure in an exhaust system. Ideally, such a method would be quick, non-invasive and well-suited for incorporation into standard manufacturing processes. Finally, it would be desirable if such a method were applicable both to green or fired ceramic structures so that the inspection method could be used both to obviate the need for firing defective green bodies, as well as to provide a final check as to the finished, fired product.

SUMMARY OF THE INVENTION

Generally speaking, the invention is a method for detecting internal discontinuities or inhomogeneities in a fired or green ceramic honeycomb structure that obviates or at least ameliorates all of the shortcomings associated with prior art testing methods. To this end, a method of determining internal discontinuities or inhomogeneities in a green (preferably dried green) or fired ceramic honeycomb structure is provided which comprises the steps of positioning an ultrasonic transmitter adjacent to, but not in contact with, the honeycomb structure, propagating an ultrasonic wave into the honeycomb structure, and receiving a response of the propagated ultrasonic wave as modulated by the structure.

Noise present in the response signal is then removed to produce a filtered response signal, which is in turn analyzed to determine the presence or absence of internal discontinuities or inhomogeneities.

Preferably, the transmitter is actuated to generate an ultrasonic wave of less than about 5 MHz so that the resulting ultrasonic wave that is conducted through the honeycomb structure has a relatively high signal-to-noise ratio. More preferably, the transmitter generates an ultrasonic wave of between about 150 and 700 KHz, and most preferably between 150 and 500 KHz.

The aforementioned ultrasonic frequencies are particularly useful in sharply resolving discontinuities in ceramic honeycomb structures formed from a ceramic material selected from the group consisting of cordierite, silicon carbide, mullite, and aluminum titanate, having a porosity ranging between about 15% to 85%, and more preferably between about 20% to 55%. The method is useful in detecting either axially-oriented cracks, or ring-off cracks within the network of web walls, as well as separations between the web walls and the outer skin. The method is also capable of detecting surface scratches and deformations as well as internal inhomogenieties, such as porosity variations.

The ultrasonic transmitter and receiver may be positioned in a non-contact position closely adjacent to the outer walls of the structure. After the first filtered response signal has been analyzed, the ultrasonic transmitter and receiver are re-located relative to the honeycomb structure and actuated again so that any internal discontinuities or inhomogeneities are ultimately detected. In lieu of sequential relocation of a single ultrasonic transmitter and receiver, arrays of ultrasonic transmitters and receivers may be used to more quickly "scan" the entire ceramic body to determine the presence or absence of any discontinuities or inhomogeneities. In a preferred method of the invention, an array of ultrasonic transmitters and receivers are positioned adjacent to, but not in contact with, the outer walls of the ceramic honeycomb so that the honeycomb may be quickly and efficiently scanned for defects.

According to further embodiments, the invention further encompasses a device for implementing the non-contact, scanning method of the invention which comprises an array of ultrasonic transmitters adjacent to, but not in contact with, the honeycomb structure, and an array of ultrasonic receivers opposite the array of ultrasonic transmitters for receiving the ultrasonic waves propagated through the structure. The array of ultrasonic transmitters and array of ultrasonic receivers may be located opposite one another, and the device may include a conveyor belt or other means for moving the ceramic honeycomb structure between the two arrays.

DESCRIPTION OF THE DRAWINGS

FIG. 2A is a schematic diagram of the application of the contact through-transmission ultrasonic testing method of the invention as applied to a flow-through ceramic substrate.

FIG. 2B is a schematic diagram of the contact through-transmission embodiment of the method as applied to a plugged substrate used as a particulate filter.

DETAILED DESCRIPTION OF THE PREFERRED EMBODIMENT

Figure 1A:
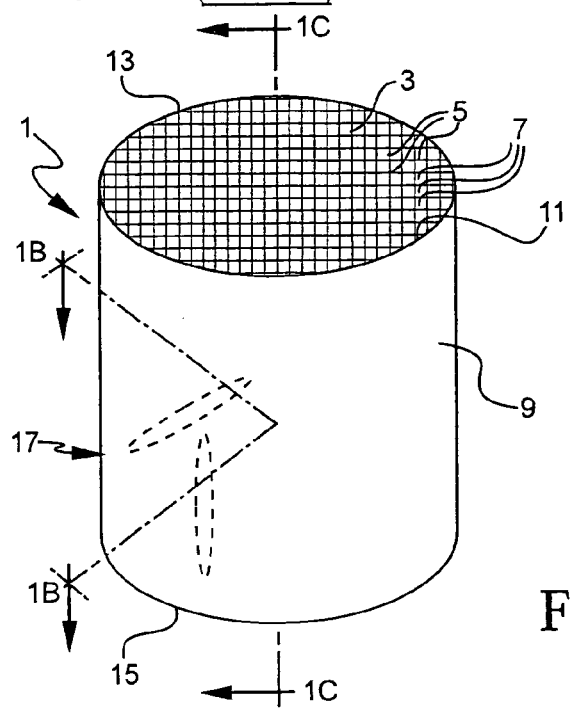
FIG. 1A is a perspective view of a prior art catalytic, flow-through ceramic substrate having internal discontinuities.
Figure 1B:
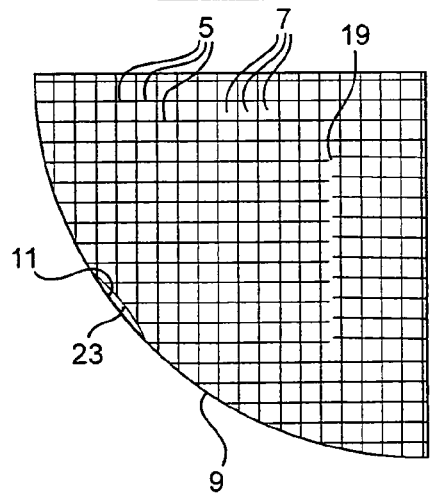
FIG. 1B is a plan, partial (¼ section) view of the ceramic substrate of FIG. 1A along the line 1B-1B.
Figure 1C:
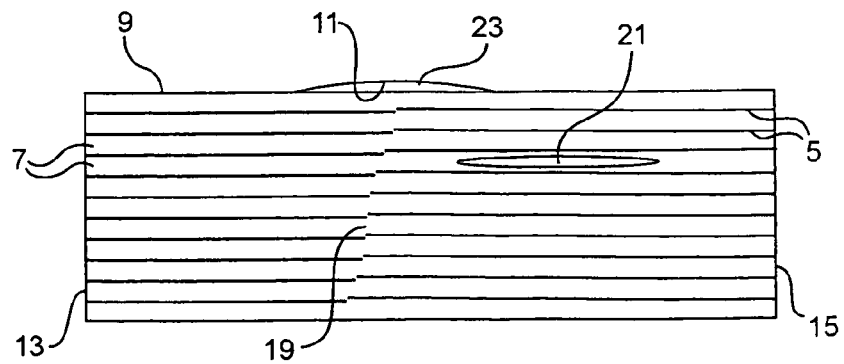
FIG. 1C is a partial side cross-sectional view of the ceramic substrate of FIG. 1A along the line 1C-1C.

With reference now to FIGS. 1A, 1B and 1C, both the method and the device of the invention are particularly useful in detecting discontinuities and other inhomogenieties which may be present in a ceramic honeycomb structure 1 of the type used in diesel and automotive exhaust systems. Such structures include a network 3 of web walls 5 that define gas-conducting cells 7 along the axis of rotation of the structure 1. The network 3 of web walls 5 is surrounded by an outer skin 9. The outer skin 9 has an inner edge 11 that is generally integrally connected (except, for example, at defects) to the outer edges of the network 3 of walls 5, as is best seen in FIG. 1B. The resulting can-shaped structure has an inlet end 13 for receiving exhaust gases from a diesel engine or automobile engine, and an outlet end 15 for expelling these gases.

Ceramic honeycomb structures 1 used as flow-through catalyst substrates have cells 7 which are completely open between the inlet and outlet ends 13, 15. The density of the cells 7 may be between approximately 100-900 cells per square inch, for example. Cell density may be maximized in order to maximize the area of contact between the automotive exhaust gases which blow directly through the gas conducting cell 7, and the web walls 5. To reduce the pressure drop that the flow-through substrate 1 imposes on the exhaust gases, the web walls 5 are typically rendered quite thin, i.e. on the order of 2-10 mils, or even 2-6 mils.

When such honeycomb structures 1 are used as wall-flow filters, such as diesel particulate filters, the open ends of the cell 7 at the inlet and outlet ends 13, 15 are plugged in a "checkerboard" pattern to force the diesel exhaust gases to pass through the porous web walls 5 before exiting the outlet end 15. The density of the cells 7 is lower than in substrates used as catalytic character, i.e. typically between about 100 and 400 cells per square inch, for example, and the web walls 5 are generally thicker, on the order of 10-25 mils thick, or even 12-16 mils thick, for example. Whether the structure 1 is used as a catalytic carrier or a particulate filter, the outer skin 9 is approximately four times as thick as the web walls 5.

Such structures 1 are manufactured by extruding a plasticized ceramic forming precursor of cordierite, mullite, silicon carbide or aluminum titanate through an extrusion die. The extruded "green body" is then cut and dried. Such green bodies are quite fragile, and must be transported to a kiln, where the resultant heat transforms the relatively soft and fragile green body into a hardened, fired honeycomb.

Unfortunately, the extrusion process and the subsequent necessary handling or processing (including cutting and firing) of the resulting, fragile green body can cause discontinuities and inhomogenieties 17 to occur in the interior of the structure 1. Even after the green body is fired, the relatively thin, brittle walls of the honeycomb structure can crack in response to mechanical shock and pressure. Such discontinuities 17 may include ring-off cracks 19 which are oriented transverse to the axis of rotation of the structure 1, and axial cracks 21 which are oriented parallel to this axis. Additionally, separations 23 can occur between the outside edges of the network 3 of web walls 5, and the inner edge 11 of the outer skin 9 can also occur. When the resulting structure 1 is used as a particulate filter, such discontinuities 17 may allow exhaust gases to flow completely through the structure 1 without filtration. When the structure 1 is used as a catalytic carrier, such discontinuities 17 form localized areas of rapid flow that may bypass the catalytic breakdown of pollutants in the exhaust. Inhomogenieties include dimensional variations (geometry related such as wall thickness variations within the interior of the substrate, wall orientation and/or waviness), and microstructural variations such as density differences, variations in porosity, and variations in amounts of microcracking within the structure.

FIG. 2A illustrates a first embodiment of the method of the invention, as applied to a flow-through ceramic structure 25 whose cells 7 define air passageways 27 having open ends 29*a*, 29*b* at both the inlet and outlet ends 13, 15. This mode is referred to herein as a "contact through-transmission" method. In this embodiment of the method, an ultrasonic signal is sent through the web walls 5 extending between the inlet and outlet ends 13, 15. For this purpose, an ultrasonic testing device 32 is provided having a transmitting transducer 33 for transmitting ultrasonic waves 34 (designated by wavy arrows), and a receiving transducer 35 for receiving the waves 34. In this embodiment of the method, the transmitting and receiving transducers 33, 35 are maintained in opposing relationship, and in contact with the structure 25, and periodically re-located and re-actuated across the inlet and outlet ends 13, 15 of the substrate 25 such that the receiving transducer 35 periodically receives directly transmitted ultrasonic waves 34 from the transmitting transducer 33. Each time, the transducers 33, 35 are substantially directly aligned across the structure from each other. Both the transmitting and receiving transducers 33, 35 may be piezo-electric transducers of the type well known in the art. The receiving piezo-electric transducer 35 resonates in response to the ultrasonic signal 34 transmitted from the transmitting transducer 33, which causes it to generate an electric signal. This signal is in turn conducted to a digital processor 37. The digital processor 37 filters the noise in the signal 34 received by the receiving transducer 35 resulting from reflections of the ultrasonic waves 34 between the transducers 33, 35, and sends the filtered signal to a display 39. Alternatively, other suitable ultrasonic testing transducers may be employed.

The resulting combined outputs of the transmitting and receiving transducer produces a kind of linear scan across the diameter or a chord of the substrate 25. When the substrate 25 is a flow-through substrate as illustrated in FIG. 2A, the transducers 33, 35 may be actuated when the transmitting transducer 33 is directly over one of the longitudinal web walls 5 such that the wave 34 is conducted through the substrate itself.

Preferably, the ultrasonic waves 34 generated by the transmitting transducer 33 are less than about 5 MHz in frequency. More preferably, the frequency of the ultrasonic waves 34 for the contact through-transmission method are between about 150 and 700 KHz, and most preferably between 150 and 500 KHz. The applicants have found that when the ultrasonic waves 34 are generated within such ranges, the signal-to-noise ratio is maximized. By contrast, when higher-frequency ultrasonic radiation is used, the applicants found that the inherent porosity of the material forming the substrate 25 makes it difficult, if not impossible to resolve discontinuity 17 located in the interior of the structure 1 due the large resulting noise factor.

FIG. 2B illustrates the contact method of the invention as applied to a filter-type ceramic substrate 40. Such substrates 40 have end plugs 42 located at one end of each of the gas conducting cells 7 to define plugged passageways 43. The previously described mode of operation is also used here. Again, in this particular mode of the invention, the transmitting and receiving transducers 33, 35 are maintained in opposing relationship and sequentially relocated along a diameter or chord of the substrate 40, and sequentially actuated in order to produce a series of linear scans of the substrate 40.

Figure 2C:
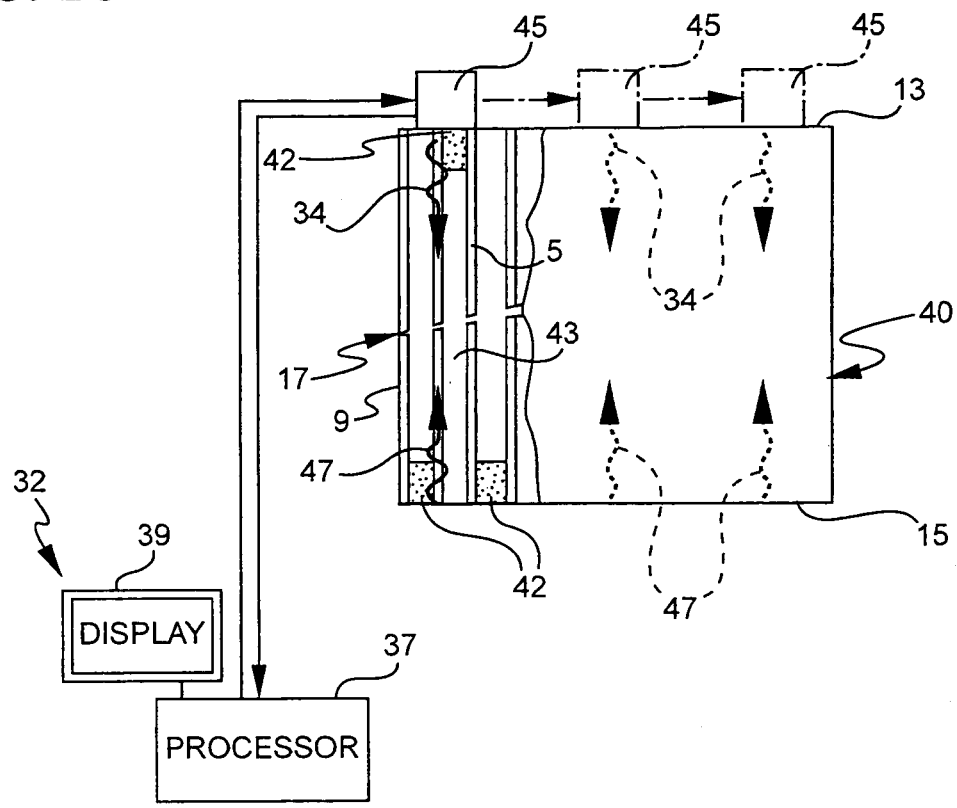
FIG. 2C is a schematic diagram of the pulse-echo embodiment of the method applied to a plugged ceramic substrate such as a particulate filter.

FIG. 2C illustrates an alternative embodiment of the method of the invention wherein the system 32 includes transmitting and receiving transducers which have been unitized into a single, ultrasonic transceiver 45 and a reflected echo of the wave is sensed. This mode is referred to herein as a "pulse echo" method. This particular embodiment of the method operates in "sonar" fashion, wherein the ultrasonic waves generated by the transceiver 45 are bounced off and reflected from the opposite end of the substrate 40. In this particular embodiment of the method, transmission is used wherein both the transmitted wave 34 and the reflected wave 47 are transmitted through the longitudinal web walls 5 of the substrate 40. In this embodiment of the method, the ultrasonic transceiver 45 placed in contact with the structure 40 at the inlet end 13 or outlet end 15 and is sequentially repositioned and re-actuated in much the same fashion as described with respect to the methods illustrated in FIGS. 2A and 2B such that a scan across the diameter or a chord of the substrate 40 is achieved. Discontinuities and/or inhomogenieties 17 such as internal cracks may be detected and located by the reflected echo using this pulse echo method. Moreover, internal homogeneities may be detected. This pulse echo method is equally applicable to filters 40 including plugs 42 as shown, but may be used for detecting discontinuities and inhomogenieties 17 in flow-through substrates as well.

The method illustrated in FIGS. 2A, 2B and 2C may be implemented by commercially available ultrasonic testing equipment (such as model number EPOCH 4 PLUS series, manufactured by Panametrics-NDT of Waltham, Mass.). Gains from 20-80 dB, preferably 40-60 dB, and filter settings of between about 100 KHz and 1 MHz and preferably 300 KHz to 800 KHz are utilized. The transmitters and receivers are preferably protective membrane transducers or dry-couplant transducers. Such transducers may have a compliant surface or elastomeric membrane which is placed in contact with the substrate. Optionally, a membrane may be placed in contact with the substrate and a gel may be applied between the membrane and a standard ultrasonic transducer used.

Figure 3A:
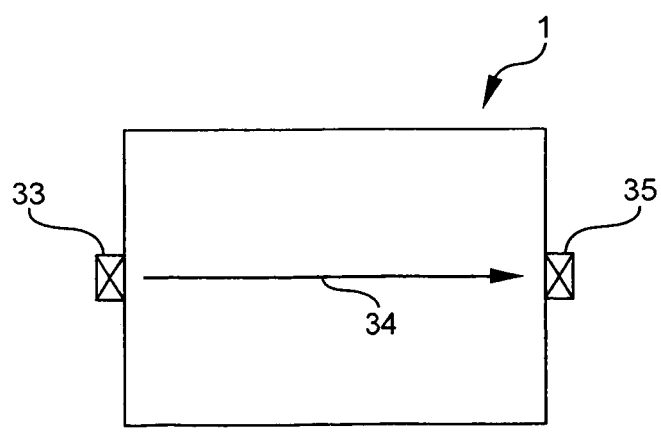
FIG. 3A is a schematic diagram illustrating the principle of the through-transmission embodiment of the method of the invention.
Figure 3B:
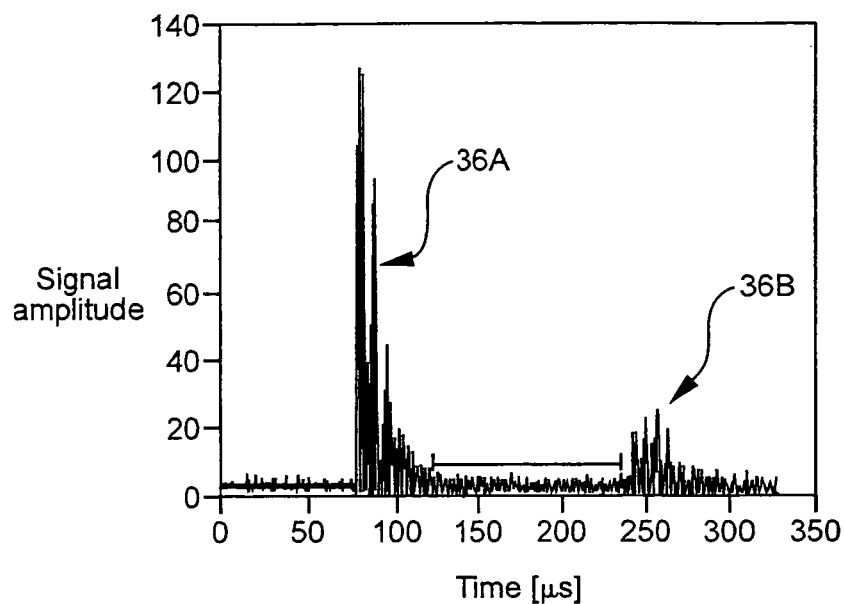
FIGS. 3B and 3C illustrate the amplitude of an ultrasonic through-wave transmitted through a substrate without internal discontinuities and a substrate with internal discontinuities, respectively.
Figure 3C:
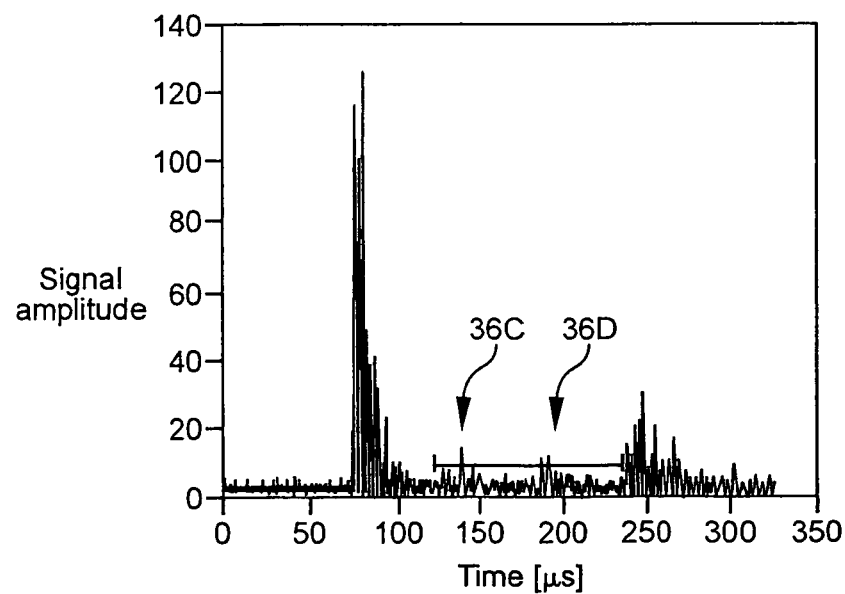
Figure 3D:
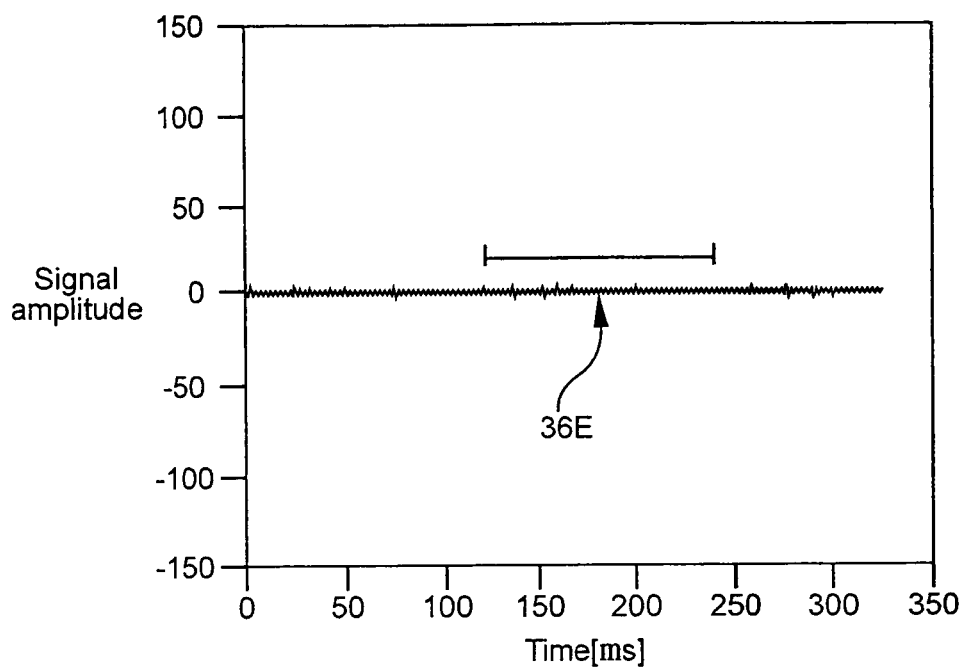
FIG. 3D illustrates the amplitude of an ultrasonic through-wave transmitted through a substrate with a large (blocking) internal discontinuity.

FIGS. 3A, 3B and 3C illustrate how the contact through-transmission embodiments of the method illustrated in FIGS. 2A and 2B operate. In particular, FIG. 3B is a graph of the amplitude of the ultrasonic wave 34 transmitted lengthwise through a substrate 1 when no discontinuity is present. As is schematically illustrated in FIG. 3A, when the transmitting transducer 33 is actuated to generate an ultrasonic wave 34, the wave is transmitted through the entire length of the substrate 1. Hence, the receiving transducer 35 registers a relatively high amplitude pulses 36A, 36B (FIG. 3B) when it receives the slightly attenuated wave 34. By contrast, when a small crack or discontinuity is present along the path between the transmitting and receiving transducers 33, 35, the trace produces in the time gate one or more peaks 36C, 36D. In that case where a significant crack or discontinuity is present in the substrate 1, as is illustrated in FIG. 3D, no high-amplitude pulse of the ultrasound wave is received or registered by the receiving transducer 35. Instead, the electric signal 36E generated by the receiving transducer 35 remains flat as shown. Hence, a flat line in the trace indicates a significant internal cracks or other defect within the substrate 1 at that tested location. Of course, by retesting at many other locations, an image of the respective tests may be assembled which provides a spatial image of any defect present.

Figure 4A:
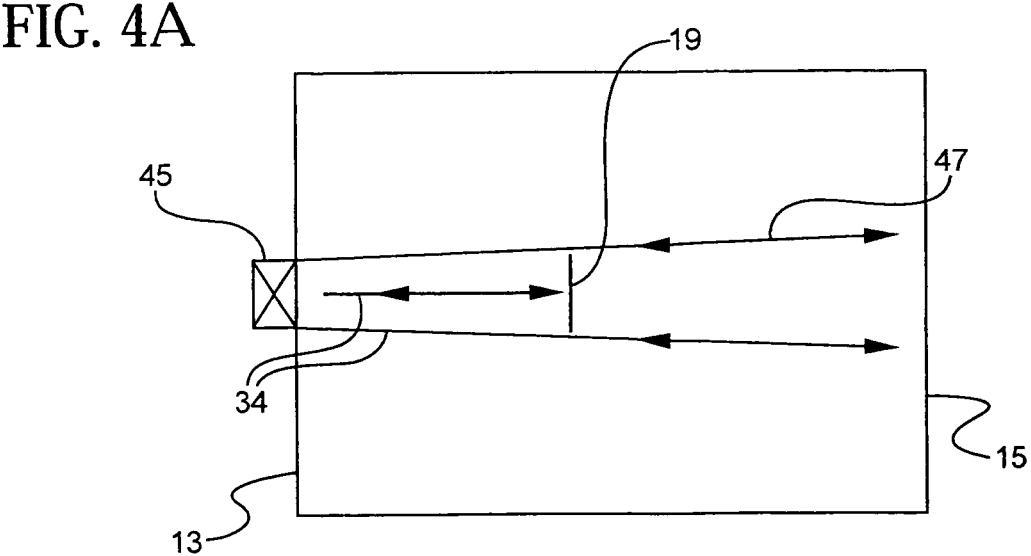
FIG. 4A is a schematic diagram illustrating the principle of the pulse echo embodiment of the method of the invention.
Figure 4B:
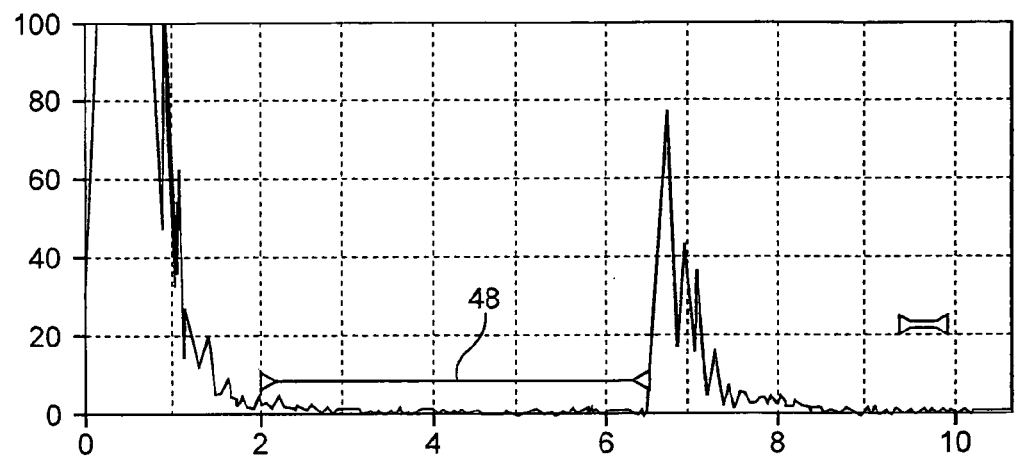
FIG. 4B is a graphical trace illustrating changes in the amplitude of a pulse echo over time for a crack-free diesel particulate filter substrate.
Figure 4C:
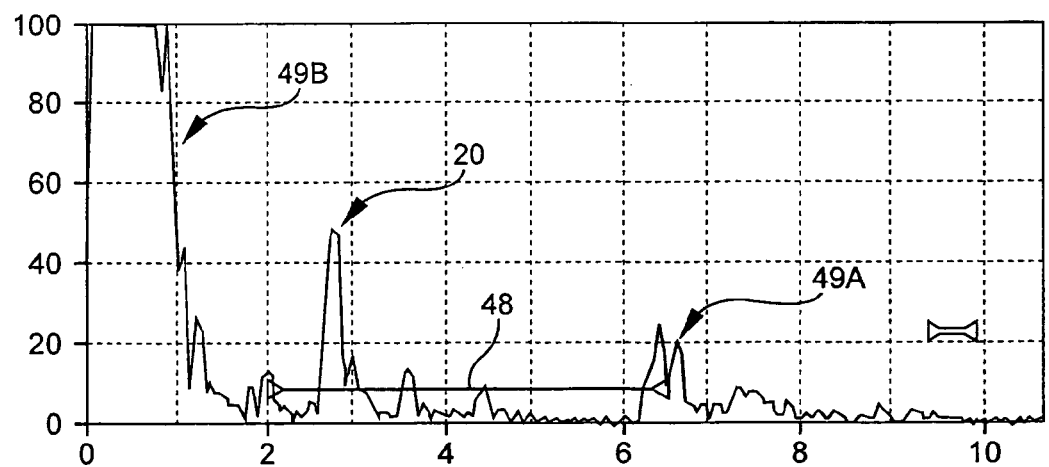
FIG. 4C is a graph illustrating changes in the amplitude of a echo over time for a diesel particulate filter having a crack.

FIGS. 4A, 4B and 4C illustrate how the pulse-echo embodiment of the method illustrated in FIG. 2C operates. When the ultrasonic transceiver 45 generates a pulse 34 of ultrasonic sound, it is transmitted from the inlet end 13 of the substrate 1 through the web walls, where it is reflected at the substrate-air interface defined by the outlet end 15. If there is no discontinuity (e.g., a crack) in the path of the wave 34, the only reflected wave 47 received by the transceiver 45 is the one reflected off the back wall of the substrate defined in this example by the outlet end 15. FIG. 4B illustrates a graphical trace of the amplitude of the received signal versus time with no cracking being evident. In particular, no peaks are evident within the time gate 48. However, when an internal crack or other discontinuity 19 is present in the pathway of the ultrasonic wave or pulse 34, the resulting reflected wave 47 generates an additional spike 20 in amplitude within the trace within the time gate 48, as is illustrated in FIG. 4C. Specifically, the reflected wave 47 generates a backwall spike 49A near the end of the graph from the ultrasonic echo reflected from the back wall of the honeycomb substrate, as well as a main bang spike 49B disposed at the left side of the graph which is indicative of reflection off the inlet face 13. One advantage of this pulse echo embodiment of the invention is that the location of the crack 19 along the axis of rotation of the cylindrical substrate 1 can be substantially determined. The relative location of the defect 19 is determined by the relative location of peak 20 within the time gate 48. In the case where a ring-off crack or discontinuity is sufficiently large, it may completely block the incident ultrasonic wave. In this instance, the reflected wave 47 may only generate the echo from the crack and no "backwall" echo such that the amplitude of backwall peak 49A will be on the order of background noise.

Figure 5A:
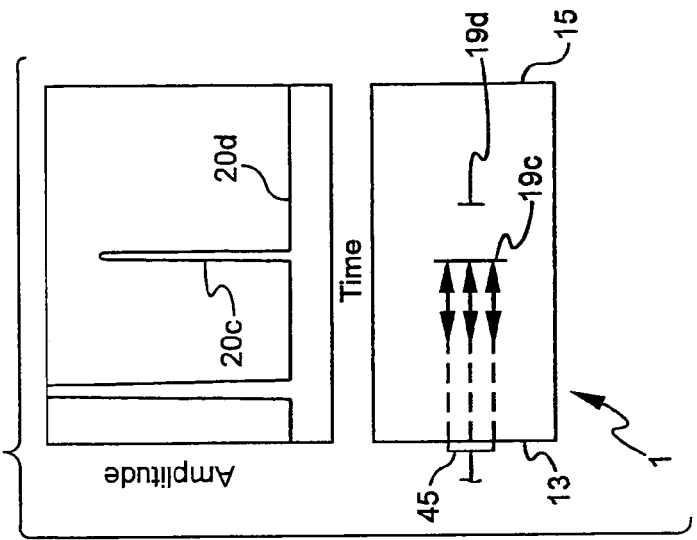
FIGS. 5A, 5B and 5C illustrate the amplitude over time graphs of pulse echo's reflected in a ceramic substrate having a single small crack, two small cracks and two cracks wherein the signature of the second crack is masked, respectively.
Figure 5B:
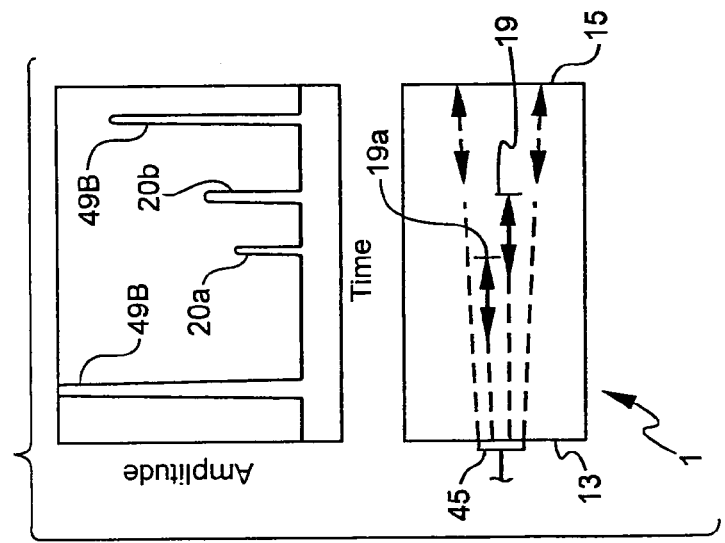
Figure 5C:
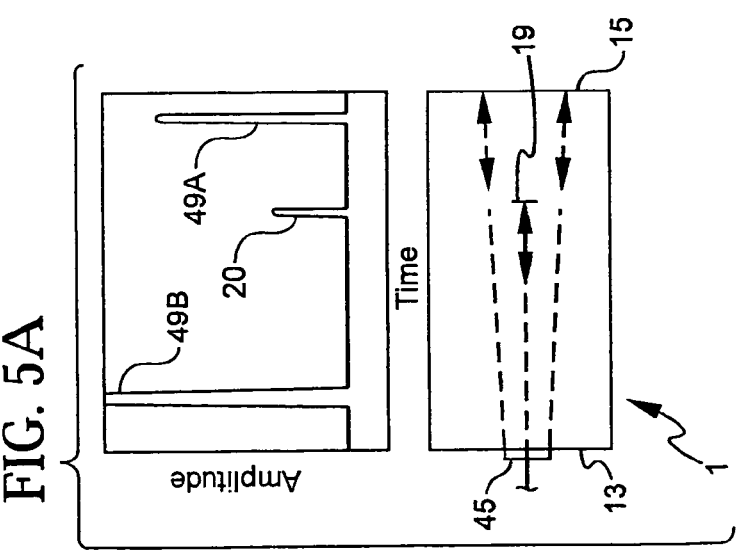

FIGS. 5A, 5B and 5C schematically illustrate the pulse echo signatures associated with different patterns of cracks or other types of discontinuities that may be present in a ceramic honeycomb substrate 1. FIG. 5A is the schematic equivalent of the pulse echo signature illustrated in FIG. 4C, wherein a single spike 20 is generated between the "main bang" pulse 49B of the ultrasonic transducer 45 and the back wall echo pulse 49A at the left and right sides of the graph, respectively. It is indicative of a single crack 19 in the honeycomb substrate 1. FIG. 5B illustrates how two different spikes 20a, 20b are generated by two different cracks 19a, 19b which are not aligned with one another along the axis of rotation of the ceramic honeycomb substrate 1. The relative amplitude of the peaks is indicative of the relative size of the two cracks 19a, 19b. Further, sonar principles can be used not only to determine the relative positions of the cracks 20a and 20b along the axis, but their absolute position as well. Their position is correlated to the relative position of the peaks 20a, 20b to the peaks 49A, 49B. Finally, FIG. 5C illustrates that, in the rare instance where a relatively larger crack 19c eclipses a smaller crack 19d along the axis of the honeycomb substrate 1, that the signature of the smaller crack 19d can be masked by the signature of the larger crack. Normally, such masking will not pose a problem in practice, as the presence of a single substantial discontinuity is sufficient for a substrate to be rejected during a quality control inspection. However, if avoidance of such undesirable masking is necessary, such avoidance may be accomplished by scanning the substrate 1 along two axes, instead of only one, i.e., from the other end.

Figure 6A:
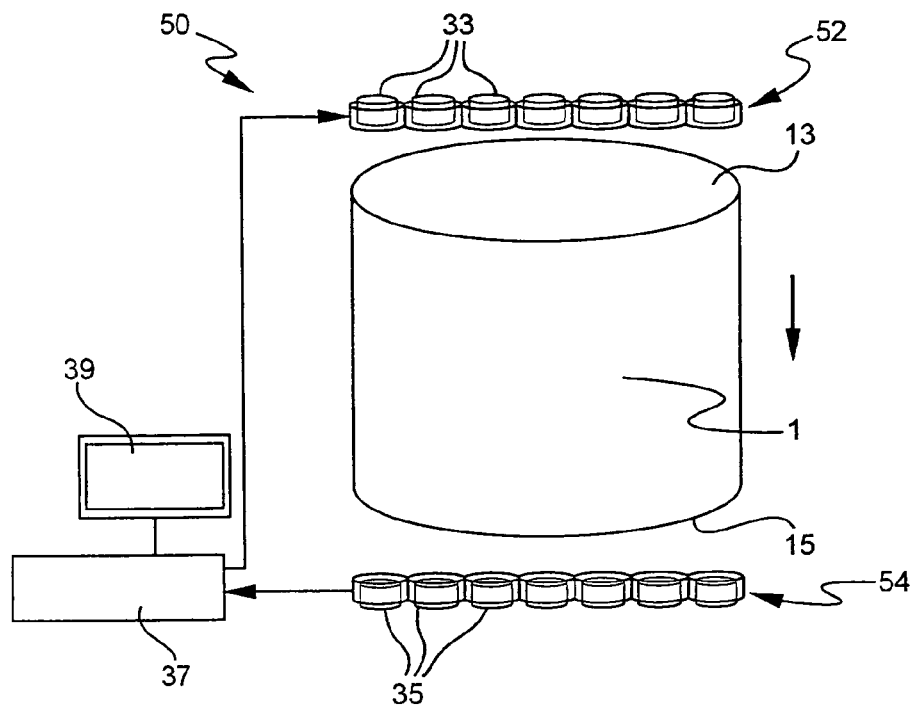
FIG. 6A is a schematic diagram of a first embodiment of the non-contact apparatus of the invention having opposing linear arrays of transmitting and receiving ultrasonic transducers for implementing a non-contact embodiment of the method.

FIG. 6A illustrates a first embodiment 50 of an apparatus of the invention which may be used to carry out the non-contact method of the invention. The method and apparatus are designed to rapidly scan the entire cross-section of a ceramic honeycomb substrate 1 in a non-contact method in a search for internal defects or inhomogenieties. The apparatus 50 includes an array or row 52 of transmitting transducers 33, arranged in opposing relationship relative to an array or row 54 of receiving transducers 35. In operation, there is relative movement between the ceramic honeycomb substrate and the upper and lower arrays 52, 54 of transmitting and receiving transducers while, at the same time, the upper row 52 of transducer transmitters periodically and simultaneously transmits waves 34 of ultrasonic pulses. For the configuration of FIG. 6A, the relative movement is in the direction into and out of the paper in successive increments wherein a new pulse is generated for each increment in the scan. The row 54 of receivers receives these waves and converts them into an electric signal which is in turn conducted to a digital processor 37. Processor 37 in turn generates a plurality of parallel graphs which together, create a complete scan of the honeycomb substrate 1 over its entire cross-section, which may then be displayed on monitor 39. In a preferred embodiment, the ceramic substrate 1 may be moved relative to the rows 52, 54 of transducer transmitters and receivers via a conveyor belt (not shown). The array of transmitters 52, 54 are preferably as large as the width of the honeycomb substrate 1, such that one sweep can provide suitable complete screening of the substrate. Of course, a smaller array may be employed with repositioning after each sweep to provide complete scan coverage.

Figure 6B:
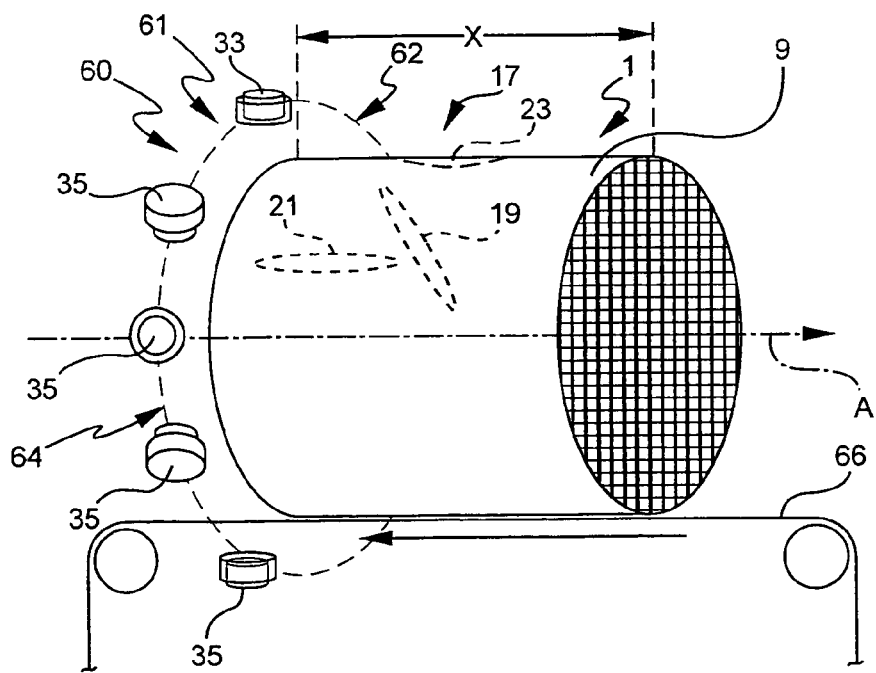
FIG. 6B is a schematic diagram of a second embodiment of the non-contact apparatus of the invention having a circular array of transmitting and receiving ultrasonic transducers for implementing a non-contact embodiment of the invention, and further illustrating the operation of this embodiment.

FIG. 6B illustrates a second embodiment 60 of the apparatus of the invention that implements a non-contact embodiment of the inventive method, which comprises an array of transducers 61 positioned radially outward from the skin 9 of the circumferential periphery of the honeycomb substrate 1, and preferably arranged in a circular pattern. The arrays 61 are preferably positioned along semicircles 62, 64 and the array 61 may include, for example, four transducer transmitters 33, and four transducer receivers 35 arranged in opposing pairs. Preferably, the transmitters 33 are positioned in the first semicircle 62, and the four receivers 35 are positioned in the second semicircle 64. The electrical inputs and outputs of the transducer array 61 are connected to a processor and display which, for simplification purposes, is not shown in FIG. 5B.

In operation, a ceramic honeycomb substrate 1 is moved through the array 61 via a conveyor belt 66 as shown such that the honeycomb substrate 1 is diametrically scanned through its circumference throughout its entire length X to determine the presence of an internal discontinuity 17, such as ring-off crack 19, an axial crack 21, and/or a skin separation 23. Of course the number of pairs may be increased or decreased depending on the size of the honeycomb substrate 1 or resolution desired. This method and apparatus may also be utilized to inspect a dried green honeycomb structure, such as a honeycomb log which includes two or more uncut lengths of the honeycomb structure therein.

Figure 6C:
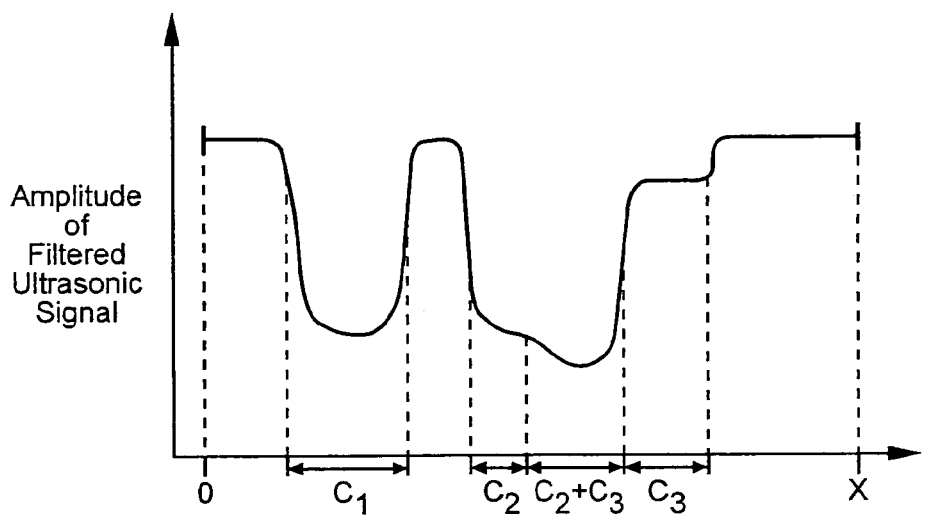
FIG. 6C is a graph illustrating variations in the amplitude of the ultrasonic signal generated by the array of FIG. 6B over the length X of a substrate containing internal discontinuities.

FIG. 6C schematically illustrates the combined output of the transducer array 61 relative to the longitudinal axis of the honeycomb substrate 1. At section C, of the graph, the portion of the honeycomb substrate 1 having an axial crack 21 is disposed within the transducer array 61, thereby attenuating the combined amplitude of the ultrasonic signal generated by the array. The amplitude rises again to the upper base line indicative of a normal internal structure until the transducer array 61 is disposed around the ring-off crack 19, and skin separation 23. As is indicated in FIG. 6C, the combined amplitude of the signal transmitted by the transducer array 61 falls in area $C_2$ as the array is aligned with the ring-off crack 19, and falls further in the area $C_2+C_3$, where the transducer array 61 simultaneously circumscribes both the ring-off crack 19, and the skin separation 23. Amplitude rises again in area $C_3$ when the array is disposed only around the skin separation 23, and then resumes to its normal baseline for the balance of the axial length X of the substrate once the circular transducer array 61 gets past the end of the skin separation 23.

Figure 7:
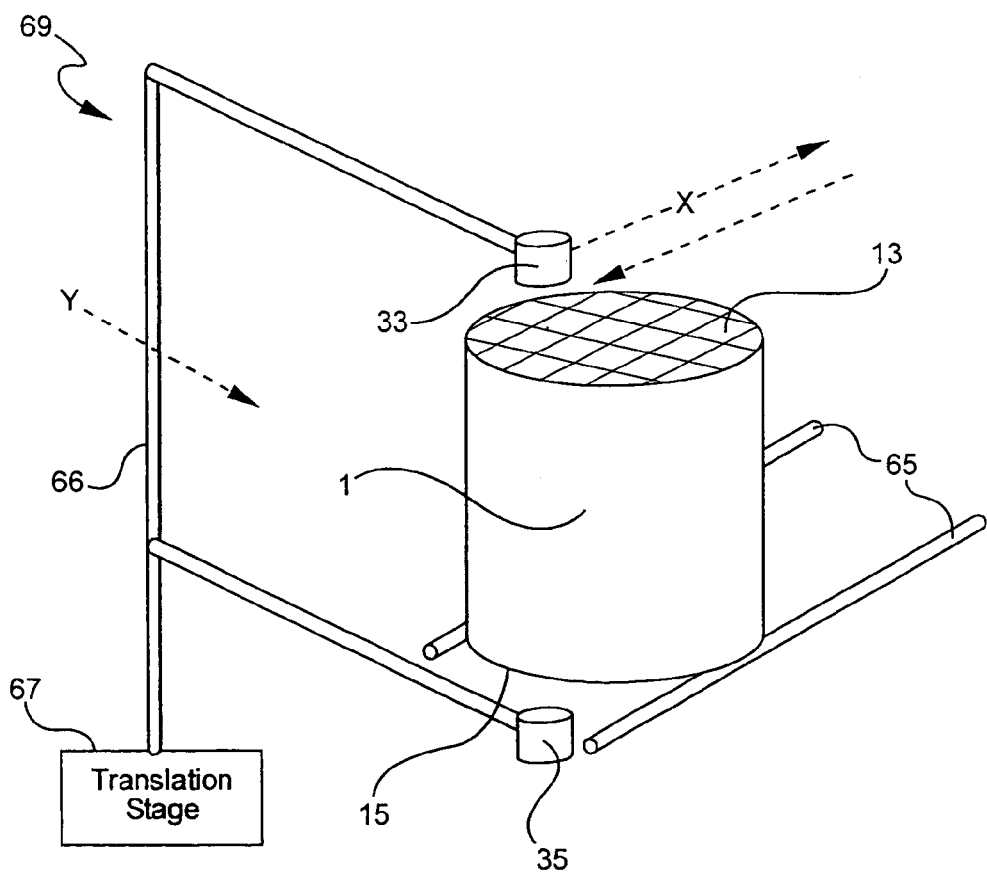
FIG. 7 is a schematic diagram of an embodiment of the non-contact test apparatus of the invention wherein two opposing ultrasonic transducers are simultaneously scanned across the ends of the substrate to detect discontinuities.

FIG. 7 schematically illustrates a third embodiment 69 of the apparatus of the invention that implements the non-contact inventive method. In this embodiment 69, the honeycomb substrate 1 is mounted on a suitable stationary platform 65, which may include two rails or other suitable fixturing, such that the inlet face 13 and the outlet face 15 are exposed. Transducer transmitter 33 and transducer receiver 35 are positioned at opposing ends of the honeycomb substrate 1 and adjacent to the inlet face 13 and outlet face 15. The transducers should be arranged in close proximity to the substrate 1, preferably near the ends 13, 15. Standoff distance between transducers 33, 35 and substrate 1 is preferably between about ½ inch (about 13 mm) to about 2 inches (about 51 mm). Both transducers 33, 35 may be mounted on a mechanical support system 66 that maintains their opposing position with respect to each other. Mechanical support system 66 may be connected to a translation stage 67 that controls the position of the transducers 33, 35 along the X and Y coordinates. From a predetermined home position the translation stage 67 may be raster scanned by actuating the stage to move the transducers 33, 35 along the X axis at a rate of about 0.01 to about 0.1 inch per second (about 0.025 mm/s to about 2.5 mm/s), and at about 0.03 to about 0.1 inch (about 0.76 mm to about 2.5 mm) increments. After the transducers 33, 35 have traversed a distance equal to or greater than the diameter of the honeycomb substrate 1, the translation stage 67 may be incremented forward at about 0.03 to 0.1 inch (about 0.76 mm to about 2.5 mm) and the process of moving across the X axis is repeated. This process continues until the entire face 13, 15 of the honeycomb substrate 1 has been scanned. The length of both the X and Y increments, and the rate of the stage movement is dependent on the required resolution.

Figure 8:
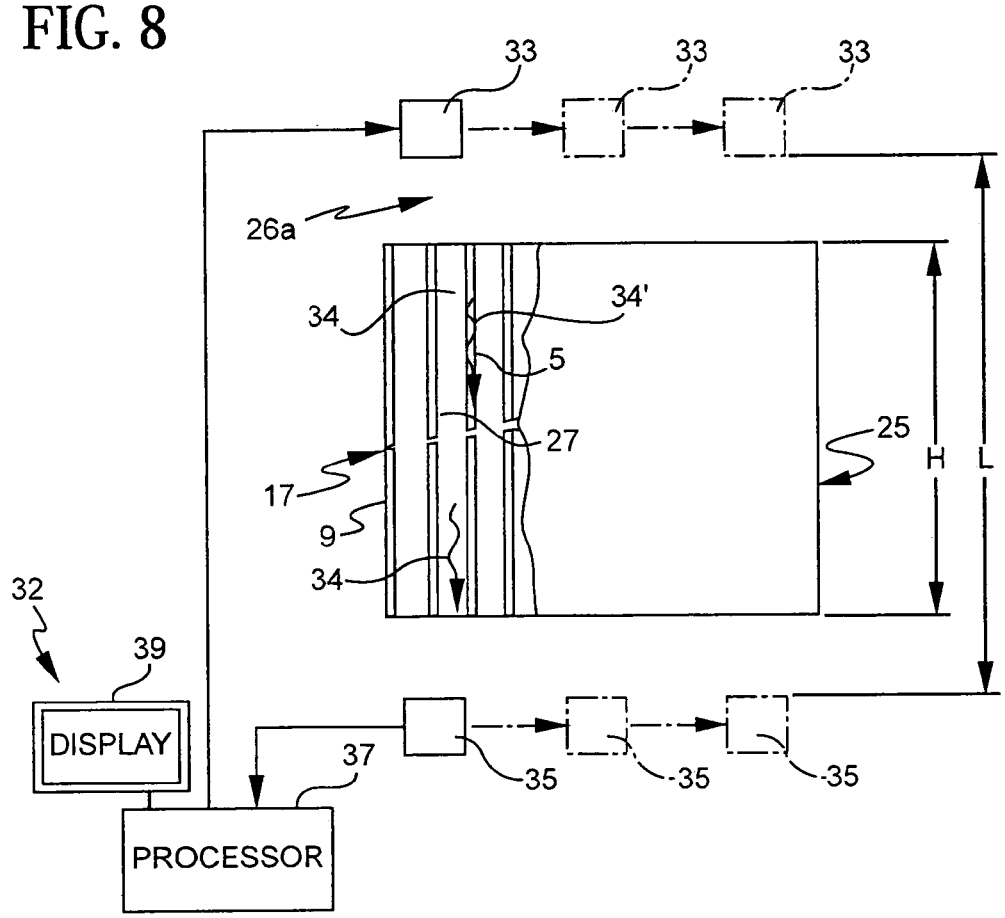
FIG. 8 is a partial cross-sectional diagram of the embodiment of the non-contact test apparatus of FIG. 7.
Figure 9A:
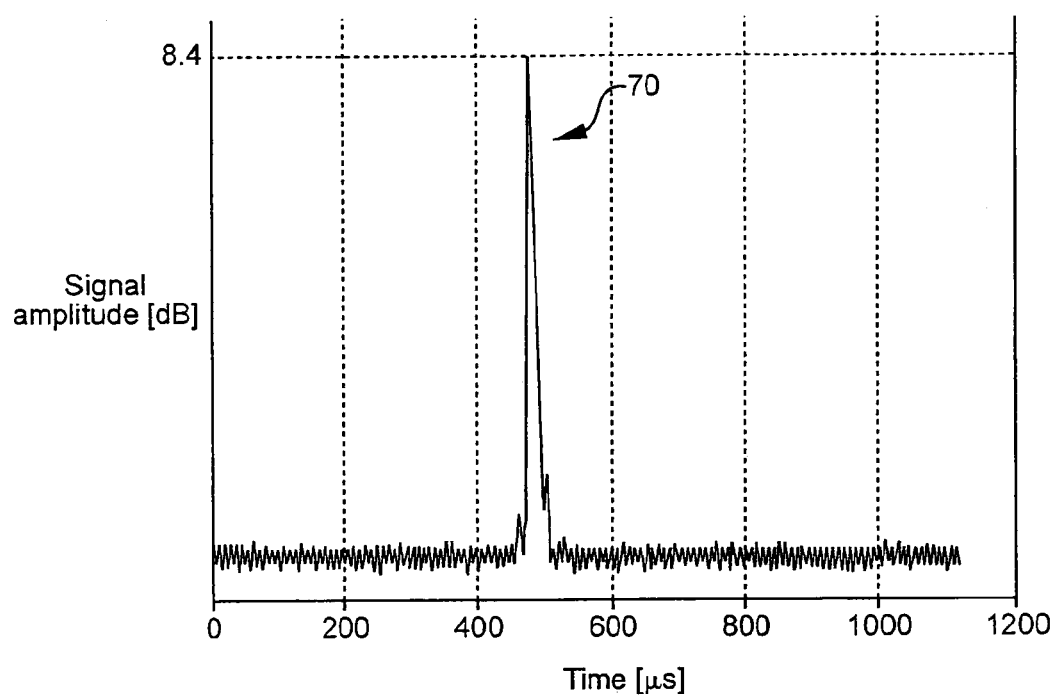
FIGS. 9A and 9B are traces illustrating signals generated from of the embodiment of the non-contact test apparatus of FIG. 7 for a flow-through substrate.

The operational method for the apparatus of FIG. 6A and FIG. 7 for flow through substrates is described with reference to FIG. 8. In operation, the transducer 33 transmits an ultrasonic wave into the air space 26a between the honeycomb substrate 25 and the transducer 33, which subsequently travels into the substrate 25. The test frequency of the wave may be at 100 KHz-1 MHz, preferably 150-700 KHz. Because of the cellular structure of the substrate 25 there are two paths, one through the air in the air passageways 27 and one through the substrate wall 5. Because the speed of sound is drastically different in the air (i.e., about 340 m/s) in the passageways 27 versus the longitudinal substrate walls 5, the processor 37 may be programmed with a targeted "gate" in the time domain to differentiate the two paths (through air 34 and through substrate wall 34') to inspect the substrate. FIG. 9A illustrates the resultant trace of the signal amplitude versus time in open air (with no substrate in the test apparatus) and shows the DTA peak 70 which is reflective of the extent of distance L (FIG. 8) between the two transducers 33, 35. The time-of-flight (TOF) for the DTA peak is given by:

$$TOF_{DTA} = L/Cair$$

Where Cair is the speed of sound in air.

Figure 9B:
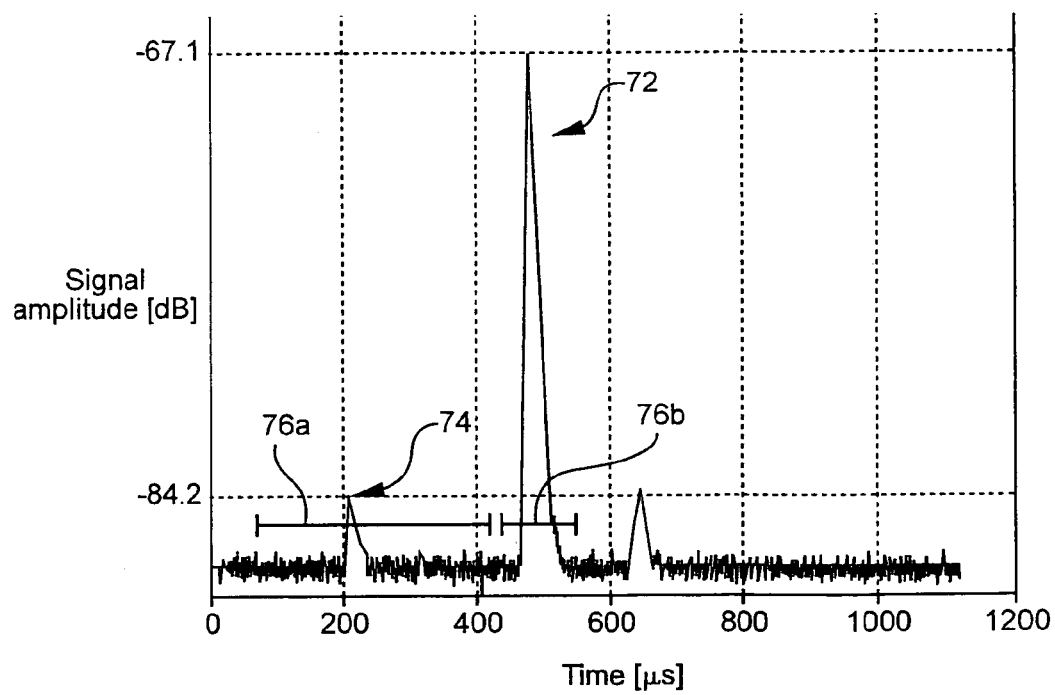

FIG. 9B illustrates the resultant trace of the signal amplitude versus time with a substrate positioned in the test apparatus. The distance H in FIG. 8 is the respective height of the substrate 25. In the trace of FIG. 9B, a modulated DTA peak 72 is shown as well as DTS peak 74. The reduced DTA peak 72 has a reduced amplitude but generally occurs at the same time as peak 70 (FIG. 9A). The time-of-flight (TOF) for the DTS peak 74 is given by:

$$T_{DTS} = (L-H)/Cair + (H/Cmat)$$

Where Cmat is the ultrasonic velocity of the substrate.

Because the speed of sound through air and through the material of the wall are dramatically different, the peaks 72, 74 will be well separated in time. To interpret the data of the traces, gates 76a, 76b may be positioned to select either the DTA signal 72 or DTS signal 74. In a honeycomb substrate inspection method, the DTS signal 74 may be used in constructing a raster scan image indicative of the discontinuity, for example. When measuring ring-off cracks or other discontinuities of the web across the axis of rotation of the structure 25, the DTS image may yield better representation of the internal defects or inhomogenieties.

Figure 10A:
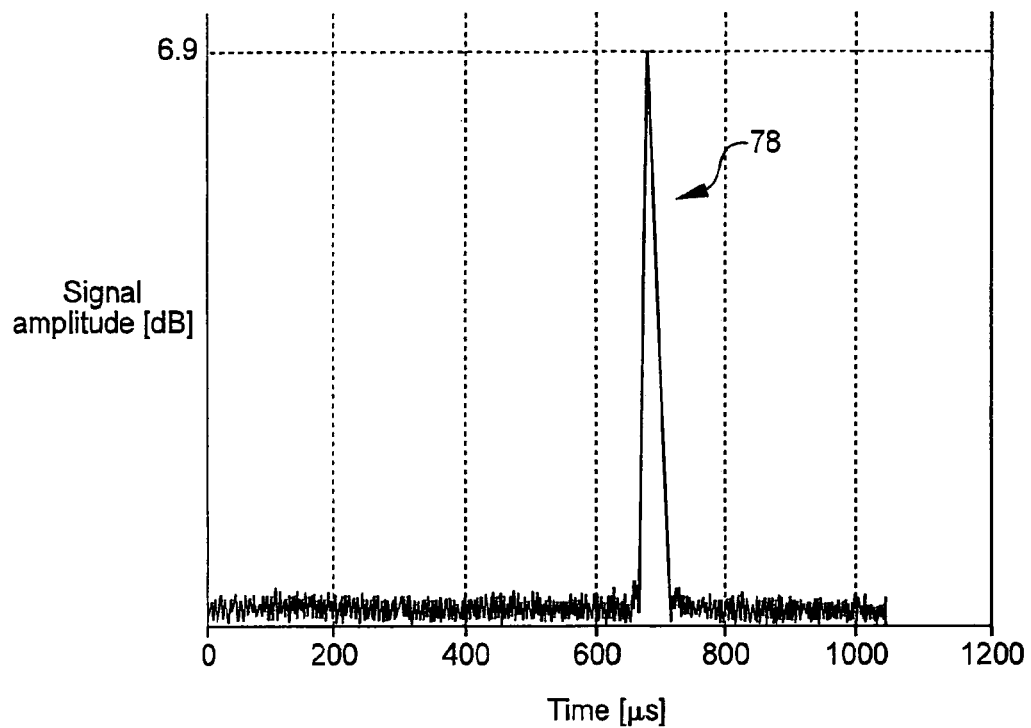
FIGS. 10A and 10B are traces illustrating signals generated from of the embodiment of the non-contact test apparatus of FIG. 7 for a honeycomb filter.
Figure 10B:
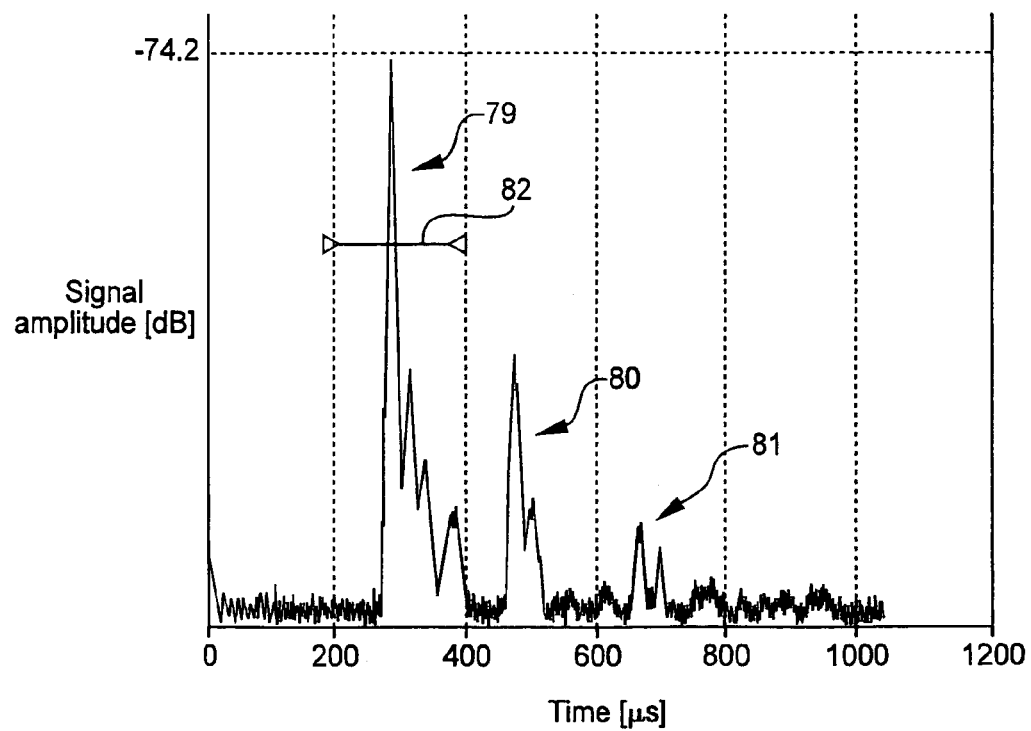

FIGS. 10A and 10B illustrate the resultant traces of signal amplitude versus time with (FIG. 10B) and without (FIG. 10B) a plugged honeycomb filter positioned in the test apparatus. FIG. 10A illustrates the resultant trace of the signal amplitude versus time in open air (with no filter in the test apparatus) and shows the open air peak 78 which is reflective of the extent of the stand off distance L (FIG. 8) between the two transducers 33, 35. In the trace of FIG. 10B, a DTS peak 79 is shown. Peaks 80 and 81 are multiple reflections from the end of the filter and may be effectively ignored. The DTS peak 79 has an amplitude which may change at various positions depending on the presence or absence of the discontinuities or inhomogenieties in the filter. For the non-contact method and apparatus, the system used must be non-contact ultrasonic test system, for example as available from VN Instruments, model SIA7 and Ultran, model iPASS. Single element transducer pairs or arrays may be used also. In the non-contact case, a broader frequency range may be employed. For example, the actuation frequency for the transducer may be between 150 KHz and 1.5 MHz, and more preferably between 200 KHz to 700 KHz.

Figure 11:
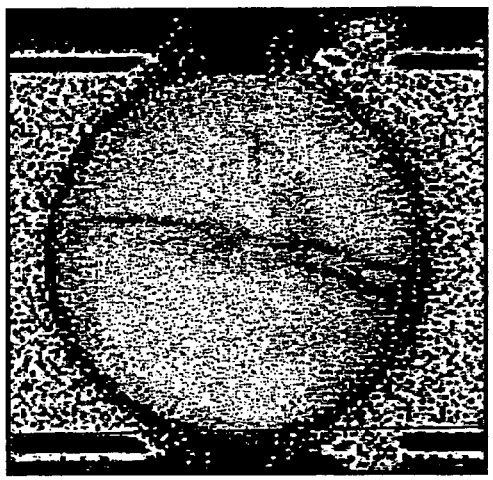
FIGS. 11 and 12 are raster scan images of the IR and TOF images, respectfully according to embodiments of the non-contact test method.
Figure 12:
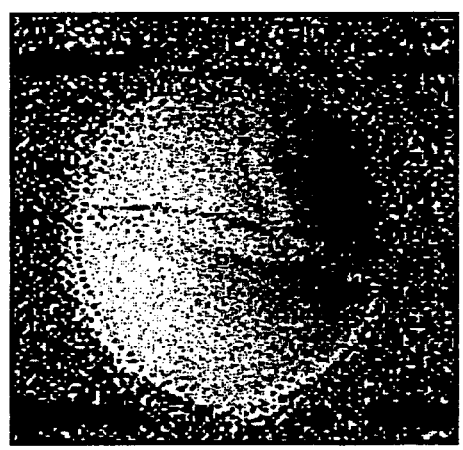

After the completion of the raster scan there may be two images created. One is an image representative of the variations of the integrated response (IR) or signal strength of the DTS signal in the substrate. The other is an image representative of the variations of the TOF of the DTS signal in the substrate. Within the raster scan image, a pattern will be developed which is indicative of an internal discontinuity or internal inhomogeniety. FIG. 11 illustrates a raster scan IR image of the DTS strength showing the presence of a branched axial crack, for example, in a cordierite honeycomb substrate having a 600/4 geometry. FIG. 12 illustrates a raster scan TOF image also showing the presence of the same branched axial crack, for example.

In the case when the DTS signal is too weak, the DTA signal 72 may be selected by the gate 76 and the same procedure described above may be employed. The relative strength of DTA vs DTS signal from the same substrate is affected by the cell density, i.e., 900/2 vs. 400/6 or 600/4, of the substrate, and the operating frequency of the ultrasonic transducer. In other words, the acoustic wavelength in air relative to the cell size and cell wall thickness affects the wave propagation, i.e., the DTS 74 or DTA 72. The best testing frequency, therefore, needs to be adjusted based on the product by performing optimizing experiments in the frequency ranges listed herein.

Because of the inherent limit of non-contact ultrasonic testing, i.e., significant acoustic impedance mismatch between air and the solid, the DTS signal is, in general, quite weak. In order to provide a sufficient signal-to-noise ratio for the DTS signal, it is preferable to have multiple signal averaging at each scan location. The resultant raster scan image, i.e., the IR or TOF image, will then more readily reveal the subtle features (cracks and/or inhomogeneities). The presence or absence of the revealed features (cracks and/or inhomogenieties) may be verified by the use of pulse echo method or through transmission methods defined herein. Accordingly, combinations of the method described herein may be utilized.

While the invention has been described with respect to several preferred embodiments, various modifications and additions will become evident to persons of skill in the art. All such additions, variations and modifications are encompassed within the scope of the invention, which is limited only by the appended claims, and equivalents thereto.

What is claimed is:

1. A method of detecting internal discontinuities or inhomogeneities in a green or fired ceramic honeycomb structure having an inlet end and an outlet end, wherein said ceramic honeycomb structure has passageways of air and passageways of substrate that define cell walls between said inlet and outlet ends, comprising the steps of:
    positioning an ultrasonic transmitter adjacent to but not in contact with one of the inlet end and outlet end of the honeycomb structure,
    actuating the ultrasonic transmitter to propagate an ultrasonic wave of between about 150 KHz and 700 KHz into said passageways in the honeycomb structure,
    receiving a response of the propagated ultrasonic wave as modulated by the structure by an ultrasonic receiver positioned opposite the ultrasonic transmitter, moving said ceramic honeycomb structure relative to said ultrasonic transmitter and said ultrasonic receiver to scan said passageways, and
    analyzing the response of the propagated ultrasonic wave to detect said internal discontinuities or inhomogeneities in said honeycomb structure,
    wherein said received response includes a distance through air signal (DTA) and a distance through substrate signal (DTS), and further comprising the step of selecting one of said DTA signal or said DTS signal to detect said internal discontinuities or inhomogeneities.

2. The method for detecting according to claim 1, further including the step of adjusting the frequency of the ultrasonic wave generated by said transmitter depending upon one or both of cell density and cell wall thickness.

3. The method for detecting according to claim 1, wherein said response is a pulse response, and further comprising the step of determining variations in one or both of the amplitude and time of flight (TOF) of said pulse response to determine the presence and position between said inlet end and said outlet end of an internal discontinuity or inhomogeneity in said honeycomb structure.

4. The method for detecting according to claim 3, further including the step of determining a size of a defect from the pulse response.

5. An apparatus for determining internal discontinuities or inhomogeneities in a green or fired ceramic honeycomb structure having an inlet end and an outlet end, comprising:
    an array of one or more ultrasonic transmitters for transmitting an ultrasonic wave of between about 150 and 700 KHz,
    a support that positions the array of transmitters adjacent to but not in contact with one of the inlet end and outlet end of the honeycomb structure for propagating ultrasonic waves into the honeycomb structure, and
    an array of ultrasonic receivers opposite the array of ultrasonic transmitters for receiving a response signal of the propagated ultrasonic waves as modulated by the structure,
    wherein said ceramic honeycomb structure has passageways of air and passageways of substrate between said inlet and outlet ends, further comprising a processor that processes both a distance through air signal (DTA) and a distance through substrate signal (DTS).

6. The apparatus of claim 5, further comprising a display that generates one or both of an image representative of variations in signal strength of said DTA signal or said DTS signal, and an image representative of variations in a time of flight (TOF) of said DTA signal or said DTS signal.

* * * * *